United States Patent [19]

O'Sullivan

[11] Patent Number: 4,753,942

[45] Date of Patent: Jun. 28, 1988

[54] METHOD FOR THE TREATMENT OF INFLAMMATORY CONDITIONS

[76] Inventor: Donncha O'Sullivan, 6 Greenfield Crescent, Donnybrook, Dublin 4, Ireland

[21] Appl. No.: 943,317

[22] Filed: Dec. 16, 1986

[30] Foreign Application Priority Data

Dec. 18, 1985 [IE] Ireland ................................. 3206/85

[51] Int. Cl.$^4$ ........................................... A61K 31/495
[52] U.S. Cl. .................................... 514/255; 514/925
[58] Field of Search ............................... 514/925, 255

[56] References Cited

U.S. PATENT DOCUMENTS 4,473,569  9/1984  O'Sullivan .......................... 424/81
4,544,656  10/1985  O'Sullivan .......................... 424/81

OTHER PUBLICATIONS

Good et al, "Hydrogen Ion Buffers for Biological Research", *Biochemistry*, vol. 5, No. 2, Feb. 1966, pp. 467–477.

*Primary Examiner*—Stanley J. Friedman
*Attorney, Agent, or Firm*—Lowe, Price, LeBlanc, Becker & Shur

[57] ABSTRACT

A method of treating arthritis and rheumatism in human patients comprises the topical application to an affected part of the patient's body of at least one zwitterionic aminosulfonic acid of the kind commonly known as Good buffers. The acid is preferably made up as a pharmaceutical composition such as a cream, and applied at a dosage of 50 μg - 50 mg of the acid per day for at least 5 days, but usually several weeks.

7 Claims, No Drawings

METHOD FOR THE TREATMENT OF INFLAMMATORY CONDITIONS

FIELD OF THE INVENTION

This invention relates to a new use for certain zwitterionic aminosulfonic acids, and in particular to the use of said acids in the therapy of inflammatory conditions.

BRIEF DESCRIPTION OF THE PRIOR ART

The acids in question are known from the chemical literature as buffers useful in biological systems. Most of them are described among other compounds by Good, N et al. in Biochemistry 1966. 5, 467 and have become known as Good buffers. They have been found useful in compositions for application to surfaces (including skin) to protect the surfaces against accidental adhesion during the use of cyanoacrylate-based adhesives (U.S. Pat. No. 4,473,569). They were subsequently found to give symptomatic relief in psoriasis and related skin ailments when applied regularly to affected areas in a topical composition (U.S. Pat. No 4,544,656).

The acids are set out by name hereunder, together with (in some cases) their currently popular trivial names in parentheses:

2-(N-Morpholinyl)-ethane sulfonic acid (MES)
2-[N-[N'-(2-Hydroxyethyl)]-piperazinyl]-ethane sulfonic acid (HEPES),
3-[N-[N'-(2-Hydroxyethyl)]-piperazinyl]-propane sulfonic acid (HEPPS),
2-[N[tris-(Hydroxymethyl)]-methylamino]-ethane sulfonic acid,
2-(N-Piperazinyl)-ethane sulfonic acid,
2-(N-Piperazinyl)-propane sulfonic acid, and
N,N-bis-(2-Hydroxyethyl)-2-aminoethane sulfonic acid (BES).

The most useful of these substances for the purposes of the invention is believed to be HEPES. This buffer has a pKa value of 7.31 at 37° C. and is widely used in other fields, unconnected with the present invention, because of its ability to stabilise the pH of mammalian systems, eg in cell and tissue culture ("The Developing Role of the Zwitterionic Buffer"- Product information supplied by BDH (British Drug Houses) Chemicals Ltd.)

HEPES takes no known part in biochemical reactions, is insoluble in organic solvents and shows no penetration of biological membranes. Thus it is not a drug as ordinarily defined. It is chemically stable and non-toxic. It has been used, inter alia, in (a) the culture of human and other mammalian cells;
(b) vaccine production, eg Mycoplasma pneumoniae vaccine;
(c) cryogenic tissue storage, eg animal semen;
(d) production and storage of blood proteins, blood storage and lyophilized plasma specimen production;
(e) the culture of bacteria, and associated enzyme assay;
(f) Mycoplasma culture and identification;
(g) various studies on organ and tissue samples, eg pituitary gland culture, rabbit kidney perfusion, conger eel liver culture;
(h) in vitro systems in the fields of photosynthesis, oxidative phosphorylation and protein biosynthesis.

BRIEF SUMMARY OF THE INVENTION

It has now, surprisingly, been found that these acids have a therapeutic effect on inflammatory ailments, particularly those associated with swelling around the joints when topically administered to a sufferer from such an ailment in a therapeutic amount over a suitable period.

The invention accordingly provides a method of treating a human patient who suffers from arthritis and/or rheumatism, which method comprises the topical application of at least one of the zwitterionic aminosulfonic acids mentioned above to an affected part of the patient's body. It is of course desirable to apply the aminosulfonic acid in a therapeutically effective amount per application, over a suitable period of time.

DETAILED DESCRIPTION OF THE INVENTION

The inflammatory ailments in which said acids have been found to have a therapeutic effect include the conditions commonly grouped together under the terms arthritis and rheumatism. The effect does not appear to extend to such conditions when they result from trauma; it is restricted to conditions which appear to arise spontaneouly, and which are presumably of systemic origin.

A suitable period is a period in the range 5 days to about 6 months. A therapeutic amount, for administration over such a period, is believed to be in the range 50 $\mu$g to 50 mg per day, equivalent to half to one-fourth of that amount per application. The acid is incorporated in a pharmaceutical composition adapted for topical application, and the composition is applied to the skin on and around the affected joints once to three times a day.

Suitable pharmaceutical compositions for use in the method of the invention include creams, ointments, gels, lotions and impregnated pads, all prepared according to recognized principles of pharmaceutical formulation.

DESCRIPTION OF A PREFERRED EMBODIMENT

A typical cream for use in the performance of the invention is made up in conventional fashion from the following ingredients (percentages by weight):

(a) Stearic acid —6.0
(b) Microcrystalline wax —3.0
(c) Glyceryl monostearate —2.5
(d) Polyoxyethylene sorbitan monolaurate —12.5
(e) HEPES (see above) —1.5
(f) Water qs ad —100.0

This gives an oil-in-water emulsion of the vanishing cream type (Cream A). Ingredient (d) is commercially available under the trade designation TWEEN 20. The above cream may additionally comprise a source of copper ions such as 0.05% cupric sulfate $CuSO_4.5H_2O$ by weight (Cream B), which appears to act synergistically in conjunction with the aminosulfonic acid.

More generally, the ingredients for a typical cream may be selected from the following list, using percentage compositions, by weight of the finished creams, not exceeding the values given:

Fatty acid —12.0
Vegetable oil —6.0
Glycerol monostearate —4.0
Paraffin wax —6.0
Polyoxyethylene sorbitan monoester —15.0

Zwitterionic aminosulfonic acid —4.0
Anti-fungal agent —0.1
Water qs ad —100.0

The proportion of aminosulfonic acid is within the range 0.5% to 4% by weight of the composition.

DESCRIPTION OF CLINICAL EMBODIMENTS OF THE METHOD OF THE INVENTION

The invention will be illustrated now in its clinical aspect by means of the following specific non-limiting examples.

EXAMPLE 1

A man in his thirties had suffered from swollen and painful finger joints for over five years and, at the time of this example, was unable to flex (bend or extend) certain fingers, before treatment started. He applied Cream A (see above) once daily to the affected fingers for about three months. At the end of the treatment he had obtained full relief, full use of the fingers was restored, the swelling and pain were gone.

EXAMPLE 2

A male patient, aged 32, suffering from stiffness and tenderness in the arms and wrists, commenced twice daily topical application of Cream B to the wrist areas only on Sept. 25, 1986. The symptoms disappeared completely after two weeks.

EXAMPLE 3

A female patient aged 50+, suffering from swelling of the knuckles and joints of the hands, with discomfort and stiffness, diagnozed by her family physician as arthritis, commenced twice daily topical application of Cream B to the affected regions on July 12, 1986. On examination three months later, it was found that the swelling of the knuckles had disappeared and normal movement of the hands had returned. There was no residual pain or discomfort.

EXAMPLE 4

A female patient aged 55, suffering from the condition commonly known as "frozen shoulder", with muscular contractions causing pain and incapacity, commenced twice daily topical application of Cream B to the affected regions on Sept. 1, 1986. On examination one month later, she was found to have lost the stiffness and pain and regained normal function of the arm and shoulder.

The condition of "frozen shoulder" commonly deteriorates until surgical intervention becomes necessary. After surgery, physiotherapy is required to help regain normal arm and shoulder function.

EXAMPLE 5

A female patient aged 76, suffering from pain and stiffness in both knee joints and unable to flex the joints normally, commenced twice daily topical application of Cream B to the affeted parts on Aug. 7, 1986. On examination of this patient two weeks later, her knees were found to have recovered their full movement. The patient was also found able to walk upstairs normally without pain or discomfort.

EXAMPLE 6

A male patient aged 42, suffering from severe pain in the left hip, and receiving occasional treatment with analgesics from his family physician, commenced twice daily topical application of Cream A on Aug. 12, 1986. Two days later the patient reported that the pain had disappeared completely. Treatment was discontinued after a total of seven days. The latest report from the patient was at the end of Oct. 1986; he had had no further pain.

Thus, although more comprehensive testing is proposed, it has been demonstrated that inflammatory conditions including rheumatism and arthritis may be successfully treated by dermal absorption of the aminosulfonic acids mentioned above. The said acids are non-toxic and are not known to produce any undesirable side-effects. Accordingly they have considerable practical advantages over medicaments heretofore used for the treatment of inflammatory conditions, such as Phenylbutazone, Indoprofen, Indomethacin and related compounds, and may be safely administered to child patients.

The pharmaceutical compositions used in the performance of the invention are bland, easily applied and very well tolerated. They have been tested for skin irritancy and dermatitis potential, and have been declared to meet the requirements of the United States Federal Register.

What I claim is:

1. A method of treating a human patient who suffers from arthritis and/or rheumatism, which method comprises the topical application, to an affected part of the patient's body, of a therapeutically effective amount of at least one zwitterionic aminosulfonic acid selected from the group consisting of 2-[N-[N'-(2-Hydroxyethyl)]-piperainyl]-ethane sulfonic acid (HEPES), 3-[N-[N'-(2-Hydroxyethyl)]-piperazinyl]-propane sulfonic acid (HEPPS), 2-(N-Piperazinyl) -ethane sulfonic acid, and 2-(N-Piperazinyl)-propane sulfonic acid.

2. A method as recited in claim 1, wherein the aminosulfonic acid is 2-[N-[N'-(2-Hydroxyethyl)]-piperazinyl]-ethane sulfonic acit (HEPES).

3. A method as recited in claim 1 wherein the amount of aminosulfonic acid applied per day of treatment lies in the range 50 μg to 50 mg.

4. A method as recited in claim 1, wherein the duration of treatment is at least 5 days.

5. A method as recited in claim 1, wherein the aminosulfonic acid is incorporated in a pharmaceutical composition adapted for topical application.

6. A method as recited in claim 5, wherein the composition is presented in a form selected from the group consisting of a cream, an ointment, a gel, a lotion and an impregnated pad.

7. A method as recited in claim 6, wherein the composition is an oil-in-water emulsion of the vanishing cream type, containing the aminosulfonic acid in a proportion within the range 0.5% to 4% by weight of the composition.

* * * * *